(12) United States Patent
Baker et al.

(10) Patent No.: US 7,110,816 B2
(45) Date of Patent: *Sep. 19, 2006

(54) REDUCTION OF LEFT-VENTRICULAR OFFSET INTERACTION WITH TACHYARRHYTHMIA DETECTION

(75) Inventors: Kenneth L. Baker, Shoreview, MN (US); David L. Perschbacher, Coon Rapids, MN (US); Andrew P. Kramer, Stillwater, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 83 days.

This patent is subject to a terminal disclaimer.

(21) Appl. No.: 10/878,953

(22) Filed: Jun. 28, 2004

(65) Prior Publication Data

US 2004/0243191 A1    Dec. 2, 2004

Related U.S. Application Data (63) Continuation of application No. 10/037,444, filed on Oct. 25, 2001, now Pat. No. 6,757,562.

(51) Int. Cl.
*A61N 1/365* (2006.01)
(52) U.S. Cl. ...................................... 607/14
(58) Field of Classification Search .............. 607/4, 607/9, 14–19
See application file for complete search history.

(56) References Cited

U.S. PATENT DOCUMENTS

| | | | |
|---|---|---|---|
| 4,343,311 A | 8/1982 | Markowitz | 128/419 PG |
| 4,354,497 A | 10/1982 | Kahn | 128/419 |
| 4,686,989 A | 8/1987 | Smyth et al. | 128/419 PG |
| 4,779,617 A | 10/1988 | Whigham | 128/419 P |
| 4,928,688 A | 5/1990 | Mower | 128/419 PG |
| 4,974,589 A | 12/1990 | Sholder | 128/419 PG |
| 5,103,820 A | 4/1992 | Markowitz | 128/419 OPG |
| 5,123,412 A | 6/1992 | Betzold | 128/419 PG |
| 5,129,393 A | 7/1992 | Brumwell | 128/419 PG |
| 5,156,149 A | 10/1992 | Hudrlik | 128/419 PG |
| 5,174,289 A | 12/1992 | Cohen | 128/419 |
| 5,191,884 A | 3/1993 | Gilli et al. | 127/419 |
| 5,233,985 A | 8/1993 | Hudrlik | 607/27 |
| 5,267,560 A | 12/1993 | Cohen | 607/25 |
| 5,370,665 A | 12/1994 | Hudrlik | 607/9 |
| 5,507,782 A | 4/1996 | Kieval et al. | 607/9 |
| 5,514,161 A | 5/1996 | Limousin | 607/9 |
| 5,558,097 A | 9/1996 | Jacobson et al. | 128/705 |
| 5,584,867 A | 12/1996 | Limousin et al. | 607/9 |
| 5,653,738 A | 8/1997 | Sholder | 607/14 |
| 5,674,259 A | 10/1997 | Gray | 607/20 |

(Continued)

OTHER PUBLICATIONS

Stahmann, Jeffrey, et al., "Reduction of Interaction With Tachyarrhythmia Detection by Negative Offset Pacing", U.S. Appl. No. 10/335,072, filed Dec. 30, 2002, 29 pgs.

*Primary Examiner*—George Manuel
(74) *Attorney, Agent, or Firm*—Schwegman, Lundberg, Woessner & Kluth, P.A.

(57) ABSTRACT

A device and method for improving tachyarrhythmia detection when the ventricles are resynchronized by delivering paces to both ventricles separated by a specified offset interval. Timing of escape intervals and tachyarrhythmia detection is based upon senses from one of the ventricles designated as a rate ventricle. A reversion pacing mode is provided in order to prevent tachyarrhythmia detection from being compromised when the rate ventricle is paced after the other ventricle.

24 Claims, 2 Drawing Sheets

U.S. PATENT DOCUMENTS

| | | | |
|---|---|---|---|
| 5,792,183 A | 8/1998 | Esler .............................. 607/4 |
| 5,792,203 A | 8/1998 | Schroeppel ................... 607/30 |
| 5,797,970 A | 8/1998 | Pouvreau ....................... 607/9 |
| 5,902,324 A | 5/1999 | Thompson et al. ............ 607/9 |
| 5,935,160 A | 8/1999 | Auricchio et al. .......... 607/122 |
| 5,941,830 A | 8/1999 | Williams .................... 600/509 |
| 6,233,485 B1 | 5/2001 | Armstrong et al. ........... 607/14 |
| 6,427,084 B1 | 7/2002 | Baker et al. ................... 607/9 |
| 6,438,421 B1 | 8/2002 | Stahmann et al. ............. 607/9 |
| 6,501,988 B1 | 12/2002 | Kramer et al. ................. 607/9 |
| 6,510,343 B1 | 1/2003 | Armstrong et al. ........... 607/25 |
| 6,553,258 B1 | 4/2003 | Stahmann et al. |
| 6,553,259 B1 | 4/2003 | Mouchawar et al. .......... 607/11 |
| 6,574,506 B1 * | 6/2003 | Kramer et al. ................. 607/9 |
| 6,757,562 B1 | 6/2004 | Baker et al. |
| 6,885,890 B1 | 4/2005 | Spinelli et al. |
| 7,016,729 B1 * | 3/2006 | Stahmann et al. ............ 607/14 |
| 2002/0082654 A1 | 6/2002 | Kramer et al. ................. 607/9 |

* cited by examiner

Fig.2B

REDUCTION OF LEFT-VENTRICULAR OFFSET INTERACTION WITH TACHYARRHYTHMIA DETECTION

CROSS-REFERENCE TO RELATED APPLICATION(S)

This application is a continuation of U.S. patent application Ser. No. 10/037,444, filed on Oct. 25, 2001 now U.S. Pat. No. 6,757,562, the specification of which is incorporated herein by reference.

FIELD OF THE INVENTION

This invention pertains to methods and apparatus for cardiac rhythm management. In particular, the invention relates to methods and apparatus for providing cardiac resynchronization pacing.

BACKGROUND

Cardiac rhythm management devices are implantable devices that provide electrical stimulation to selected chambers of the heart in order to treat disorders of cardiac rhythm and include pacemakers and implantable cardioverter/defibrillators. A pacemaker is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Pacing therapy may also be applied in order to treat cardiac rhythms that are too fast, termed anti-tachycardia pacing. (As the term is used herein, a pacemaker is any cardiac rhythm management device with a pacing functionality, regardless of any other functions it may perform such as the delivery cardioversion or defibrillation shocks to terminate atrial or ventricular fibrillation.)

Also included within the concept of cardiac rhythm is the manner and degree to which the heart chambers contract during a cardiac cycle to result in the efficient pumping of blood. For example, the heart pumps more effectively when the chambers contract in a coordinated manner. The heart has specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Patients who exhibit pathology of these conduction pathways, such as bundle branch blocks, can thus suffer compromised cardiac output.

Patients with conventional pacemakers can also have compromised cardiac output because artificial pacing with an electrode fixed into an area of the myocardium does not take advantage of the above-described specialized conduction system. The spread of excitation from a single pacing site must proceed only via the much slower conducting muscle fibers of either the atria or the ventricles, resulting in the part of the myocardium stimulated by the pacing electrode contracting well before parts of the chamber located more distally to the electrode, including the myocardium of the chamber contralateral to the pacing site. Although the pumping efficiency of the heart is somewhat reduced from the optimum, most patients can still maintain more than adequate cardiac output with artificial pacing.

Heart failure is a clinical syndrome in which an abnormality of cardiac function causes cardiac output to fall below a level adequate to meet the metabolic demand of peripheral tissues and is usually referred to as congestive heart failure (CHF) due to the accompanying venous and pulmonary congestion. CHF can be due to a variety of etiologies with ischemic heart disease being the most common. Some CHF patients suffer from some degree of AV block or are chronotropically deficient such that their cardiac output can be improved with conventional bradycardia pacing. Such pacing, however, may result in some degree of uncoordination in atrial and/or ventricular contractions due to the way in which pacing excitation is spread throughout the myocardium as described above. The resulting diminishment in cardiac output may be significant in a CHF patient whose cardiac output is already compromised. Intraventricular and/or interventricular conduction defects are also commonly found in CHF patients. In order to treat these problems, cardiac rhythm management devices have been developed which provide electrical pacing stimulation to one or more heart chambers in an attempt to improve the coordination of atrial and/or ventricular contractions, termed cardiac resynchronization therapy.

SUMMARY OF THE INVENTION

Cardiac resynchronization therapy can most conveniently be delivered by a cardiac rhythm management device in accordance with a bradycardia pacing mode so that the activation patterns between and within selected heart chambers are both resynchronized and paced concurrently. One way to implement resynchronization therapy is to designate one heart chamber as the rate chamber and the contralateral chamber as the synchronized chamber and then pace both chambers with an escape interval based upon rate chamber senses. For example, the right and left ventricles may be designated as the rate and synchronization chambers, respectively, with paces delivered to both ventricles upon expiration of the escape interval. If the ventricles are paced with a negative offset interval, such that the left ventricle is paced before expiration of the escape interval when the right ventricle is paced, the lower limit rate at which a tachyarrhythmia can be detected is increased due to the presence of a cross-chamber refractory period. In one embodiment of the invention, a pace to a synchronized chamber at a pacing instant defined by the negative offset interval is inhibited when a maximum tachyarrhythmia rate threshold interval, defined as the pacing interval minus the negative offset interval, is less than a specified limit value.

DETAILED DESCRIPTION

The present invention is concerned with a method and system for delivering cardiac resynchronization pacing in a particular mode. The following is a description of the hardware used to deliver such therapy, bradycardia and resynchronization pacing in general, and exemplary embodiments of the invention.

1. Hardware Platform

Pacemakers are typically implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. Atrial and ventricular senses are also called P-waves and R-waves with reference to their representations on a surface electrocardiogram. In order to cause such a contraction in the absence of an intrinsic beat, a pacing pulse (either an atrial pace or a ventricular pace) with energy above a certain pacing threshold is delivered to the chamber.

Figure 1:
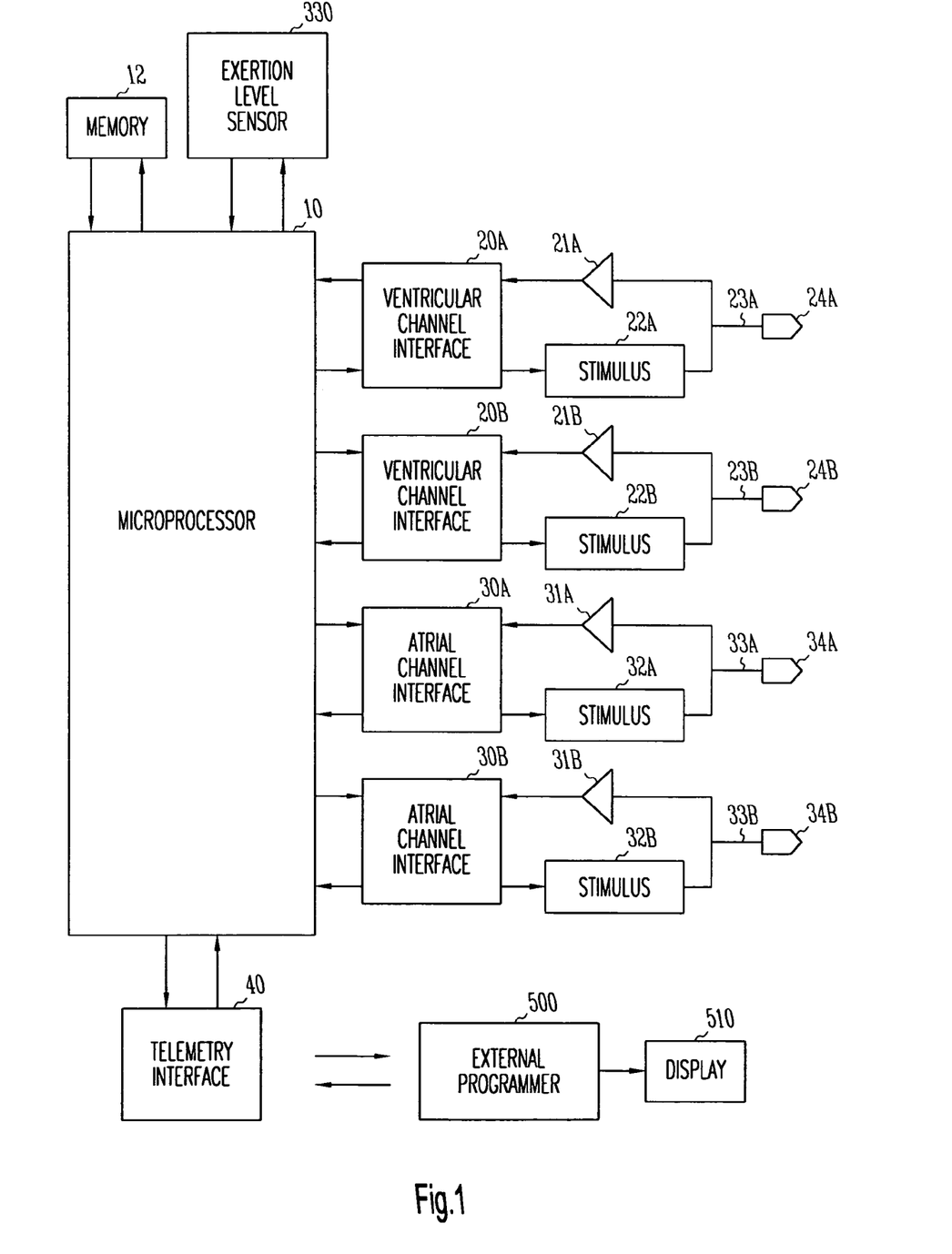
FIG. 1 is a system diagram of a pacemaker configured for resynchronization pacing.

FIG. 1 shows a system diagram of a microprocessor-based pacemaker physically configured with sensing and pacing channels for both atria and both ventricles. The controller 10 of the pacemaker is a microprocessor that communicates with a memory 12 via a bidirectional data bus. The memory 12 typically comprises a ROM (read-only memory) for program storage and a RAM (random-access memory) for data storage. The pacemaker has atrial sensing and pacing channels comprising electrode 34a–b, leads 33a–b, sensing amplifiers 31a–b, pulse generators 32a–b, and atrial channel interfaces 30a–b which communicate bidirectionally with microprocessor 10. The device also has ventricular sensing and pacing channels for both ventricles comprising electrodes 24a–b, leads 23a–b, sensing amplifiers 21a–b, pulse generators 22a–b, and ventricular channel interfaces 20a–b. In the figure, "a" designates one ventricular or atrial channel and "b" designates the channel for the contralateral chamber. In this embodiment, a single electrode is used for sensing and pacing in each channel, known as a unipolar lead. Other embodiments may employ bipolar leads that include two electrodes for outputting a pacing pulse and/or sensing intrinsic activity. The channel interfaces 20a–b and 30a–b include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. An exertion level sensor 330 (e.g., an accelerometer or a minute ventilation sensor) enables the controller to adapt the pacing rate in accordance with changes in the patient's physical activity. A telemetry interface 40 is also provided for communicating with an external programmer 500 that has an associated display 510. A pacemaker incorporating the present invention may possess all of the components in FIG. 1 and be programmable so as to operate in a number of different modes, or it may have only those components necessary to operate in a particular mode.

The controller 10 controls the overall operation of the device in accordance with programmed instructions stored in memory. The controller 10 controls the delivery of paces via the pacing channels, interprets sense signals from the sensing channels, and implements timers for defining escape intervals and sensory refractory periods. Both bradycardia and anti-tachycardia pacing modes may be implemented in code executed by the controller. In the latter, paces are delivered according to a defined protocol that acts so as to terminate a tachyarrhythmia when such a rhythm is detected by the sensing channels. As explained below, the controller may also be programmed to incorporate a reversion mode to facilitate tachyarrhythmia detection during certain biventricular pacing modes.

2. Bradycardia Pacing Modes

Bradycardia pacing modes refer to pacing algorithms used to pace the atria and/or ventricles when the intrinsic ventricular rate is inadequate either due to AV conduction blocks or sinus node dysfunction. Such modes may either be single-chamber pacing, where either an atrium or a ventricle is paced, or dual-chamber pacing in which both an atrium and a ventricle are paced. The modes are generally designated by a letter code of three positions where each letter in the code refers to a specific function of the pacemaker. The first letter refers to which heart chambers are paced and which may be an A (for atrium), a V (for ventricle), D (for both chambers), or O (for none). The second letter refers to which chambers are sensed by the pacemaker's sensing channels and uses the same letter designations as used for pacing. The third letter refers to the pacemaker's response to a sensed P wave from the atrium or an R wave from the ventricle and may be an I (for inhibited), T (for triggered), D (for dual in which both triggering and inhibition are used), and O (for no response). Modem pacemakers are typically programmable so that they can operate in any mode that the physical configuration of the device will allow. Additional sensing of physiological data allows some pacemakers to change the rate at which they pace the heart in accordance with some parameter correlated to metabolic demand. Such pacemakers are called rate-adaptive pacemakers and are designated by a fourth letter added to the three-letter code, R.

Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

In atrial tracking pacemakers (i.e., VDD or DDD mode), another ventricular escape interval is defined between atrial and ventricular events, referred to as the atrio-ventricular interval (AVI). The atrio-ventricular interval is triggered by an atrial sense or pace and stopped by a ventricular sense or pace. A ventricular pace is delivered upon expiration of the atrio-ventricular interval if no ventricular sense occurs before. Atrial-tracking ventricular pacing attempts to maintain the atrio-ventricular synchrony occurring with physiological beats whereby atrial contractions augment diastolic filling of the ventricles. If a patient has a physiologically normal atrial rhythm, atrial-tracking pacing also allows the ventricular pacing rate to be responsive to the metabolic needs of the body.

A pacemaker can also be configured to pace the atria on an inhibited demand basis. An atrial escape interval is then defined as the maximum time interval in which an atrial sense must be detected after a ventricular sense or pace before an atrial pace will be delivered. When atrial inhibited demand pacing is combined with atrial-triggered ventricular demand pacing (i.e., DDD mode), the lower rate interval is then the sum of the atrial escape interval and the atrio-ventricular interval.

Finally, rate-adaptive algorithms may be used in conjunction with bradycardia pacing modes. Rate-adaptive pacemakers modulate the ventricular and/or atrial escape intervals based upon measurements corresponding to physical activity. Such pacemakers are applicable to situations in which atrial tracking modes cannot be used. In a rate-adaptive pacemaker operating in a ventricular pacing mode, the LRL is adjusted in accordance with exertion level measurements such as from an accelerometer or minute ventilation sensor in order for the heart rate to more nearly match metabolic demand. The adjusted LRL is then termed the sensor-indicated rate.

3. Cardiac Resynchronization Therapy

Cardiac resynchronization therapy is pacing stimulation applied to one or more heart chambers in a manner that restores or maintains synchronized bilateral contractions of the atria and/or ventricles and thereby improves pumping efficiency. Certain patients with conduction abnormalities may experience improved cardiac synchronization with conventional single-chamber or dual-chamber pacing as described above. For example, a patient with left bundle branch block may have a more coordinated contraction of the ventricles with a pace than as a result of an intrinsic contraction. In that sense, conventional bradycardia pacing of an atrium and/or a ventricle may be considered as resynchronization therapy. Resynchronization pacing, however, may also involve pacing in accordance with a synchronized pacing mode as described below.

It is advantageous to deliver resynchronization therapy in conjunction with one or more synchronous bradycardia pacing modes, such as are described above. Resynchronization therapy may then be implemented by adding synchronized pacing to the bradycardia pacing mode where paces are delivered to one or more synchronized pacing sites in a defined time relation to one or more selected sensing and pacing events that either reset escape intervals or trigger paces in the bradycardia pacing mode. One heart chamber is designated as the rate chamber, and the heart chamber contralateral to the rate chamber is designated as a synchronized chamber. For example, the right ventricle may be designated as the rate ventricle with the left ventricle designated as the synchronized ventricle, and the paired atria may be similarly designated. The synchronized chamber is then paced with an inhibited demand pacing mode using an escape interval that is reset by a sense occurring in the contralateral rate chamber or a pace delivered to either chamber.

One synchronized pacing mode may be termed offset synchronized pacing. In this mode, the synchronized chamber is paced with a positive, negative, or zero timing offset as measured from a pace delivered to its paired rate chamber, referred to as the synchronized chamber offset interval. The offset interval may be zero in order to pace both chambers simultaneously, positive in order to pace the synchronized chamber after the rate chamber, or negative to pace the synchronized chamber before the rate chamber. One example of such pacing is biventricular offset synchronized pacing where both ventricles are paced with a specified offset interval. The rate ventricle is paced in accordance with a synchronous bradycardia mode, which may include atrial tracking, and the ventricular escape interval is reset with either a pace or a sense in the rate ventricle. (Resetting in this context refers to restarting the interval in the case of an LRL ventricular escape interval and to stopping the interval in the case of an AVI.) Thus, a pair of ventricular paces are delivered after expiration of the AVI escape interval or expiration of the LRL escape interval, with ventricular pacing inhibited by a sense in the rate ventricle that restarts the LRL escape interval and stops the AVI escape interval.

As mentioned above, certain patients may experience some cardiac resynchronization from the pacing of only one ventricle and/or one atrium with a conventional bradycardia pacing mode. It may be desirable, however, to pace a single atrium or ventricle in accordance with a pacing mode based upon senses from the contralateral chamber. This mode, termed synchronized chamber-only pacing, involves pacing only the synchronized chamber based upon senses from the rate chamber. One way to implement synchronized chamber-only pacing is to pseudo-pace the rate chamber whenever the synchronized chamber is paced before the rate chamber is paced, such that the pseudo-pace inhibits a rate chamber pace and resets any rate chamber escape intervals. Such pseudo-pacing can be combined with the offset synchronized pacing mode using a negative offset to pace the synchronized chamber before the rate chamber and thus pseudo-pace the rate chamber, which inhibits the real scheduled rate chamber pace and resets the rate chamber pacing escape intervals. Sensed events in the rate chamber will thus inhibit the synchronized chamber-only pacing, which may benefit some patients by preventing pacing that competes with intrinsic activation (i.e., fusion beats). In order to prevent pacing the synchronized chamber during its vulnerable period, a synchronized chamber pace may be inhibited if a synchronized chamber sense occurs within a protection period prior to expiration of the rate chamber escape interval. Since the synchronized chamber pace is inhibited by the protection period, the rate chamber is not pseudo-paced and, if no intrinsic activity is sensed in the rate chamber, it will be paced upon expiration of the rate chamber escape intervals. The rate chamber pace in this situation may thus be termed a safety pace. For example, in left ventricle-only synchronized pacing, a right ventricular safety pace is delivered if the left ventricular pace is inhibited by the left ventricular protection period and no right ventricular sense has occurred.

An example of synchronized chamber-only pacing is left ventricle-only synchronized pacing where the rate and synchronized chambers are the right and left ventricles, respectively. Left ventricle-only synchronized pacing may be advantageous where the conduction velocities within the ventricles are such that pacing only the left ventricle results in a more coordinated contraction by the ventricles than with conventional right ventricular pacing or biventricular pacing. Left ventricle-only synchronized pacing may be implemented in inhibited demand pacing modes with or without atrial tracking. A left ventricular pace is then delivered upon expiration of the AVI escape interval or expiration of the LRL escape interval, with left ventricular pacing inhibited by a right ventricular sense that restarts the LRL escape interval and stops the AVI escape interval.

4. Interaction of Resynchronization Pacing with Tachyarrhythmia Detection

Even while pacing the heart in a bradycardia resynchronization pacing mode, modern cardiac rhythm management devices still monitor intrinsic cardiac activity for the onset of tachyarrhythmias. The device detects an atrial or ventricular tachyarrhythmia by measuring the time interval between successive atrial or ventricular depolarizations, respectively, and comparing the measured interval to a specified limit value. That limit value is referred to as the tachyarrhythmia rate threshold interval (TRTI) and corresponds to the lowest intrinsic rate that is to be regarded as a tachyarrhythmia, referred to as the tachyarrhythmia rate threshold (TRT). The device thus detects a tachyarrhythmia when a measured interval between intrinsic senses is below the tachyarrhythmia rate threshold interval. Other processing on signals received from the sensing channels may also be performed to further characterize the tachyarrhythmia. Some devices may record the onset of a tachyarrhythmia in a log that can be downloaded by a clinician later to aid in diagnosis and further treatment planning, and other devices may initiate therapy such as anti-tachycardia pacing or cardioversion/defibrillation upon detection of a tachyarrhythmia.

Figure 2A:
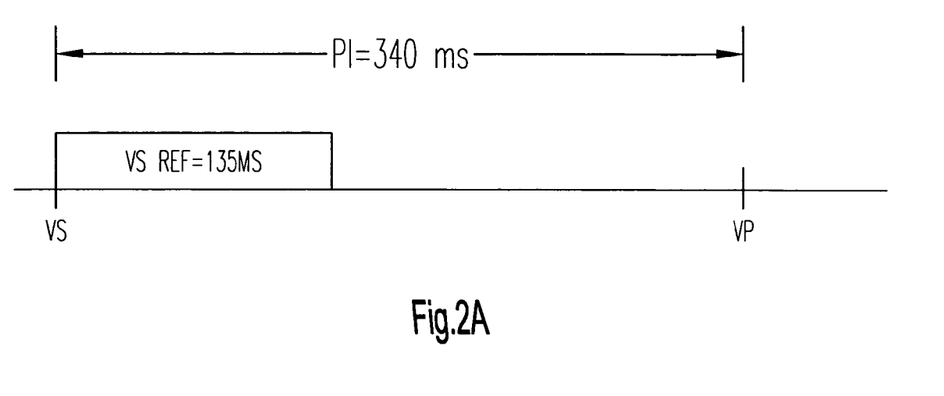
FIGS. 2A–2B are timing diagrams illustrating how tachyarrhythmia detection is affected by ventricular pacing.

Pacing the heart in a demand mode, however, necessarily affects the upper and lower rates of a tachyarrhythmia that can be detected. FIG. 2A illustrates the situation with an exemplary timing diagram that depicts ventricular paces VP and ventricular senses VS that occur when the ventricles are paced in a demand mode. Sensing channels in a cardiac rhythm management device are rendered refractory after a sense is detected in order to prevent the misinterpretation of input data by the sensing of afterpotentials or by crosstalk between sensing channels. The ventricular sensing channel in FIG. 2A is rendered refractory after a ventricular sense for a refractory period VS Ref during which no ventricular senses can be detected for purposes of detecting a tachyarrhythmia. The highest rate tachyarrhythmia that can be detected is determined by the length of this refractory period since an intrinsic rhythm with an R-R interval shorter than the refractory period will always have at least one beat occurring while the sensing channel is refractory. In the example of FIG. 2A, the period VS Ref is 135 milliseconds so that the highest tachyarrhythmia rate that can be detected is 60,000/135=444 bpm. The lowest rate tachyarrhythmia that can be detected while pacing the ventricles in a demand mode is determined by the pacing interval since only an intrinsic rate with an R—R interval shorter than the pacing interval is allowed to occur. The pacing interval is the time between a previous ventricular pace or sense that initiates an escape interval and the next ventricular pace. In univentricular pacing, or biventricular pacing with a zero or positive offset, the pacing interval is equal to the escape interval that causes the subsequent ventricular pace, where the escape interval may be either a ventricular escape interval or an atrio-ventricular interval in the case of an atrial tracking mode. In the example of FIG. 2A, the pacing interval PI is 340 milliseconds so that the lowest tachyarrhythmia that can be detected is equal to the pacing rate of 60,000/340=175 bpm. A pacemaker can be programmed such that the escape intervals used to pace the ventricles, which may change due to atrial tracking or due to a rate-adaptive mode that modulates the ventricular escape interval in accordance with an exertion level measurement, is constrained to never drop below an interval that would result in a pacing rate that is greater than the lowest tachyarrhythmia rate that is desired to be detectable (i.e., the TRT). That is, the maximum allowable pacing rate is made less than or equal to the tachyarrhythmia rate threshold or, equivalently, the minimum interval between successive escape interval expirations is made greater than or equal to the tachyarrhythmia rate threshold interval.

Sensing channels are also rendered refractory after paces are delivered in order to prevent reentry into the system of an output pacing pulse. The refractory period may be made up of a blanking interval, during which the sensing amplifiers are blanked and no signals are received, and/or a software implemented refractory period during which received signals are simply ignored by the device. The refractory period thus prevents a far-field sense due to a pace from being counted for purposes of detecting a tachyarrhythmia. When paces are only delivered at a pacing instant that coincides with expiration of an escape interval, tachyarrhythmia detection is unaffected by a sensing refractory period that starts after a pace since a rhythm with an R—R interval shorter than the pacing interval will prevent further pacing. In certain resynchronization pacing modes as described above, however, paces may be delivered at a pacing instant that does not coincide with expiration of an escape interval. In offset synchronized pacing with a negative offset interval, the rate chamber is paced upon expiration of an escape interval, but a preceding pace is delivered to the synchronized chamber at a pacing instant defined by the negative offset interval. The escape interval is reset by a rate chamber pace or a rate chamber sense, and rate chamber senses are normally used for tachyarrhythmia detection. If a cross-chamber refractory period for the rate chamber sensing channel is initiated upon delivery of a pace to the synchronized chamber, no rate chamber sensing occurs for the duration of the period even though the escape interval has not yet expired. This has the effect of making the lowest detectable tachyarrhythmia rate greater than the pacing rate.

Figure 2B:
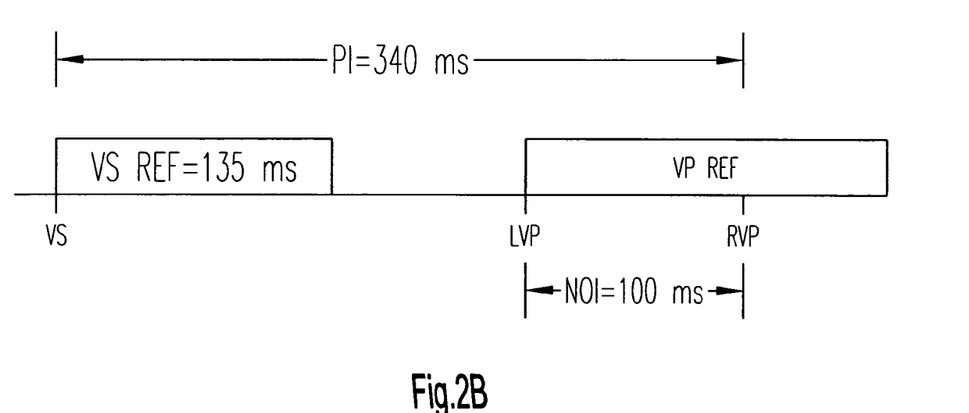

FIG. 2B illustrates the effect of a cross-chamber refractory period in the case of biventricular offset pacing with a negative offset interval where the left and right ventricles are the synchronized and rate chambers, respectively. A left ventricular pace LVP thus precedes a right ventricular pace RVP by the negative offset interval. The pacing interval PI is 340 milliseconds, the refractory period starting after a ventricular sense is 135 milliseconds, and the negative offset interval is 100 milliseconds. As in the example of FIG. 2A, the highest tachyarrhythmia rate that can be detected is 444 bpm. The lowest detectable tachyarrhythmia rate in this case, however, is greater than the pacing rate of 175 bpm due to the cross-chamber refractory period VP Ref that starts after the left ventricular pace. Because the refractory period VP Ref starts 100 milliseconds before expiration of the escape interval, the effective lower limit on the tachyarrhythmia rate threshold is the reciprocal of the pacing interval minus the negative offset interval or 240 milliseconds, resulting in a lower limit for tachyarrhythmia detection of 60,000/240=250 bpm.

For example, the controller of the device illustrated in FIG. 1 may be programmed to deliver biventricular negative offset pacing to right and left ventricles designated as rate and synchronized chambers, respectively. The controller is further programmed to detect a tachyarrhythmia when a time interval between successive rate chamber senses is below a specified tachyarrhythmia rate threshold interval TRTI. The synchronized and rate chambers are paced with a negative offset such that the rate chamber is paced upon expiration of an escape interval and a preceding pace is delivered to the synchronized chamber at a pacing instant defined by a negative offset interval, with the escape interval being reset by a rate chamber pace or a rate chamber sense. The rate chamber sensing channel is rendered refractory for a selected cross-chamber sensing refractory period upon delivery of a synchronized chamber pace. The pacing interval, defined as the time interval from an immediately preceding rate chamber sense or pace to expiration of either an atrio-ventricular or ventricular escape interval, may be constrained to be no shorter than a desired tachyarrhythmia rate threshold interval. As explained above, the programmed tachyarrhythmia rate threshold interval TRTI may be compromised when the pacing rate increases above a certain value due to atrial tracking or rate-adaptive pacing. This interaction between negative offset pacing and tachyarrhythmia detection may be reduced or eliminated, however, by programming the controller to modify the operation of the device in accordance with the invention as detailed below.

In order to decrease the lower limit for tachyarrhythmia detection during synchronized offset pacing with a negative offset interval, a reversion mode may be provided if the pacing rate is increased to a point where the desired lower limit rate for tachyarrhythmia detection would otherwise be compromised. The effective lower limit for tachyarrhythmia detection corresponds to a maximum tachyarrhythmia rate threshold interval MTRTI that may be expressed in terms of the pacing interval PI and the negative offset interval NOI as:

$$MTRTI = PI - NOI$$

where the pacing interval PI is the interval between a preceding ventricular sense or pace that initiates a ventricular escape interval and the next expiration of an escape interval causing a ventricular pace, either the ventricular escape interval or an atrio-ventricular interval. In the reversion mode, a synchronized chamber pace is inhibited at the pacing instant defined by the negative offset interval if the maximum tachyarrhythmia rate threshold interval MTRTI decreases below a specified limit value. For example, the specified limit value may correspond to the desired tachyarrhythmia rate threshold interval TRTI or to some higher value in order to provide a safety margin. After the synchronized chamber pace is inhibited at the pacing instant defined by the negative offset interval, a synchronized chamber pace may either: 1) be delivered at the expiration of the escape interval, whereupon either no pace is delivered to the rate chamber or a pace is simultaneously delivered to the rate chamber with the synchronized chamber pace, 2) not delivered for that cardiac cycle so that only the rate chamber is paced upon expiration of the escape interval, or 3) be delivered before expiration of the escape interval at a time interval measured from an immediately preceding rate chamber sense or pace equal to the desired tachyarrhythmia rate threshold interval. Alternatively, rather than inhibiting the synchronized chamber pace at the pacing instant defined by the negative offset interval, the negative offset interval may be decreased if the maximum tachyarrhythmia rate threshold interval MTRTI would decrease below a specified limit value if the negative offset interval were left unchanged. The negative offset interval is decreased so as to be equal to or less than the pacing interval minus the specified tachyarrhythmia rate threshold interval and is then returned to its original value during subsequent cardiac cycles if the MTRTI increases above the specified limit value.

The reversion modes just described thus have the effect of maintaining a desired tachyarrhythmia rate threshold TRT even during periods of rapid pacing in an offset synchronized pacing mode with a negative offset. Other ways of maintaining the TRT in this situation are also possible. For example, the negative offset interval may be dynamically varied as a function of rate. The negative offset is thus varied, linearly or otherwise, from a specified maximum value to a specified minimum value as the pacing rate varies from minimum to maximum values. In the case of ventricular pacing, for example, the negative offset interval is varied as the ventricular pacing rate varies from the lower rate limit or LRL to the maximum allowable pacing rate. Another way to maintain the TRT is to keep the negative offset fixed but limit the maximum allowable pacing rate that the device will allow to be programmed once the desired tachyarrhythmia rate threshold TRT is set. In that case, the maximum allowable pacing rate MPR is constrained to be equal to or less than the reciprocal of the desired tachyarrhythmia rate threshold interval TRTI plus the negative offset interval NOI:

$$MPR \leq 1/(TRTI + NOI)$$

Instead of maintaining a desired TRT as the pacing rate increases, another type of reversion mode may be employed to lower the TRT to a specified value when a single tachyarrhythmic interval is detected, making the device capable of detecting lower rate tachyarrhythmias. In such a reversion mode, when an interval between a sense or pace and a subsequent sense is below a specified first tachyarrhythmia rate threshold interval, the device may be programmed to lower the TRT by increasing the pacing interval to be equal to or greater than a specified second tachyarrhythmia rate threshold interval plus the negative offset interval. The pacing interval is increased by increasing the ventricular escape interval and/or the atrio-ventricular interval.

Yet another way of dealing with the compromise of the desired tachyarrhythmia rate threshold TRT by a negative offset interval is to recognize that some fraction of intrinsic depolarizations occurring at a rate above the TRT will be missed when the pacing rate exceeds the reciprocal of the desired tachyarrhythmia rate threshold interval TRTI plus the negative offset interval NOI. Thus, under normal circumstances, a tachyarrhythmia may be declared when some proportion of successive detected ventricular depolarizations, e.g., eight out of ten, have intervals below the TRTI. If the desired TRT is compromised by a high pacing rate, the criteria for recognizing a tachyarrhythmia may then be modified so as to require a lower proportion of successive detected ventricular depolarizations for declaration of a tachyarrhythmia, e.g., five out of ten.

As explained above, the effect of offset synchronized ventricular pacing with a negative offset interval on tachyarrhythmia detection is brought about by the synchronized ventricle being paced before the rate ventricle, with senses from the latter also being used for tachyarrhythmia detection. Another alternative for reducing the interaction between negative offset pacing and tachyarrhythmia detection is to interchange the rate and synchronized ventricles if the pacing rate exceeds a specified limit value. Although it may be desirable for the right ventricle to be used as the rate ventricle under normal circumstances, this arrangement can be changed in order to maintain a desired TRT while still pacing the left ventricle before the right. In that case, the left ventricle becomes the rate ventricle and is also used for tachyarrhythmia detection, and the negative offset interval becomes a positive offset interval.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A cardiac rhythm management device, comprising:
a sensing channel for sensing depolarizations from a heart chamber designated as the rate chamber, wherein the heart chamber contralateral to the rate chamber is designated as the synchronized chamber;
a controller for controlling the delivery of paces in accordance with a programmed pacing mode;
wherein the controller is programmed to:
detect a tachyarrhythmia when a time interval between successive rate chamber senses is below a specified tachyarrhythmia rate threshold interval;
pace the synchronized and rate chambers with a negative offset such that the rate chamber is paced after the synchronized chamber upon expiration of an escape interval and a preceding pace is delivered to the synchronized chamber at a pacing instant defined by a negative offset interval, wherein the escape interval is reset by a rate chamber pace or a rate chamber sense and wherein a pacing interval, defined as the interval between a rate chamber pace or sense and expiration of an escape interval, is constrained by a specified maximum pacing rate to be no shorter than the specified tachyarrhythmia rate threshold interval;
render the rate chamber sensing channel refractory for a selected cross-chamber sensing refractory period upon delivery of a synchronized chamber pace during which no sensing of rate chamber events occurs; and,
inhibit a synchronized chamber pace at the pacing instant defined by the negative offset interval and deliver a pace to at least one of the chambers upon expiration of the escape interval when a maximum tachyarrhythmia rate threshold interval, defined as the pacing interval minus the negative offset interval, is less than a specified limit value.

2. The device of claim 1 wherein the specified limit value is the specified tachyarrhythmia rate threshold interval plus a specified safety margin.

3. The device of claim 1 wherein the controller is programmed to deliver the synchronized chamber pace at the expiration of the escape interval, with a pace being simultaneously delivered to the rate chamber with the synchronized chamber pace, whenever the synchronized chamber pace is inhibited at the pacing instant defined by the negative offset interval.

4. The device of claim 1 wherein the controller is programmed to deliver the synchronized chamber pace at the expiration of the escape interval, with no pace being delivered to the rate chamber with the synchronized chamber pace, whenever the synchronized chamber pace is inhibited at the pacing instant defined by the negative offset interval.

5. The device of claim 1 wherein the controller is programmed to deliver no pace to the synchronized chamber and pace only the rate chamber upon expiration of the escape interval whenever the synchronized chamber pace is inhibited at the pacing instant defined by the negative offset interval.

6. The device of claim 1 wherein the controller is programmed to deliver a synchronized chamber pace before expiration of the escape interval and at a time interval measured from an immediately preceding rate chamber sense or pace equal to the specified tachyarrhythmia rate threshold interval whenever the synchronized chamber pace is inhibited at the pacing instant defined by the negative offset interval.

7. The device of claim 1 wherein the rate and synchronized chambers are the right and left ventricles, respectively, and wherein the controller is programmed to pace the rate and synchronized ventricles in accordance with a ventricular demand pacing mode such that the escape interval is a ventricular escape interval.

8. The device of claim 7 further comprising an exertion level sensor wherein the controller is programmed to modulate the ventricular escape interval in accordance with input from the exertion level sensor.

9. The device of claim 1 further comprising an atrial sensing channel and wherein the controller is programmed to pace the ventricles in accordance with an atrial tracking mode such the escape interval is an atrio-ventricular interval.

10. A cardiac rhythm management device, comprising:
a sensing channel for sensing depolarizations from a heart chamber designated as the rate chamber, wherein the heart chamber contralateral to the rate chamber is designated as the synchronized chamber;
a controller for controlling the delivery of paces in accordance with a programmed pacing mode;
wherein the controller is programmed to:
detect a tachyarrhythmia when a time interval between successive rate chamber senses is below a specified tachyarrhythmia rate threshold interval;
pace the synchronized and rate chambers with a negative offset such that the rate chamber is paced upon expiration of an escape interval and a preceding pace is delivered to the synchronized chamber at a pacing instant defined by a negative offset interval, wherein the escape interval is reset by a rate chamber pace or a rate chamber sense and wherein a pacing interval, defined as the interval between a rate chamber pace or sense and expiration of an escape interval, is constrained by a specified maximum pacing rate to be no shorter than the specified tachyarrhythmia rate threshold interval;
render the rate chamber sensing channel refractory for a selected cross-chamber sensing refractory period upon delivery of a synchronized chamber pace during which no sensing of rate chamber events occurs; and,
decrease the negative offset interval to a value that is equal to or less than the pacing interval minus the specified tachyarrhythmia rate threshold interval when a maximum tachyarrhythmia rate threshold interval, defined as the pacing interval minus the negative offset interval, is less than a specified limit value.

11. A cardiac rhythm management device, comprising:
a sensing channel for sensing depolarizations from a heart chamber designated as the rate chamber, wherein the heart chamber contralateral to the rate chamber is designated as the synchronized chamber;
a controller for controlling the delivery of paces in accordance with a programmed pacing mode;
wherein the controller is programmed to:
detect a tachyarrhythmia when a time interval between successive rate chamber senses is below a specified tachyarrhythmia rate threshold interval;
pace the synchronized and rate chambers with a negative offset such that the rate chamber is paced upon expiration of an escape interval and a preceding pace is delivered to the synchronized chamber at a pacing instant defined by a negative offset interval, wherein the escape interval is reset by a rate chamber pace or a rate chamber sense and wherein a pacing interval, defined as the interval between a rate chamber pace or sense and expiration of an escape interval, is constrained by a specified maximum pacing rate to be no shorter than the specified tachyarrhythmia rate threshold interval;
render the rate chamber sensing channel refractory for a selected cross-chamber sensing refractory period upon delivery of a synchronized chamber pace during which no sensing of rate chamber events occurs; and,
vary the negative offset from a maximum specified value to a minimum specified value as the pacing rate, defined as the reciprocal of the pacing interval, varies from a specified minimum value to the specified maximum pacing rate.

12. A cardiac rhythm management device, comprising:
a sensing channel for sensing depolarizations from a heart chamber designated as the rate chamber, wherein the heart chamber contralateral to the rate chamber is designated as the synchronized chamber;
a controller for controlling the delivery of paces in accordance with a programmed pacing mode;
wherein the controller is programmed to:
detect a tachyarrhythmia when a time interval between successive rate chamber senses is below a specified tachyarrhythmia rate threshold interval;
pace the synchronized and rate chambers with a negative offset such that the rate chamber is paced upon expiration of an escape interval and a preceding pace is delivered to the synchronized chamber at a pacing instant defined by a negative offset interval, wherein the escape interval is reset by a rate chamber pace or a rate chamber sense and wherein a pacing interval, defined as the interval between a rate chamber pace or sense and expiration of an escape interval, is constrained by a specified maximum pacing rate to be no shorter than the specified tachyarrhythmia rate threshold interval;
render the rate chamber sensing channel refractory for a selected cross-chamber sensing refractory period upon delivery of a synchronized chamber pace during which no sensing of rate chamber events occurs; and,
limit the specified maximum pacing rate that the device will allow to be programmed, once the specified tachyarrhythmia rate threshold is programmed, to be equal to or less than the reciprocal of the specified tachyarrhythmia rate threshold interval plus the negative offset interval.

13. A cardiac rhythm management device, comprising:
a sensing channel for sensing depolarizations from a heart chamber designated as the rate chamber, wherein the heart chamber contralateral to the rate chamber is designated as the synchronized chamber;
a controller for controlling the delivery of paces in accordance with a programmed pacing mode;
wherein the controller is programmed to:
detect a tachyarrhythmia when a time interval between successive rate chamber senses is below a specified tachyarrhythmia rate threshold interval;
pace the synchronized and rate chambers with a negative offset such that the rate chamber is paced upon expiration of an escape interval and a preceding pace is delivered to the synchronized chamber at a pacing instant defined by a negative offset interval, wherein the escape interval is reset by a rate chamber pace or a rate chamber sense and wherein a pacing interval, defined as the interval between a rate chamber pace or sense and expiration of an escape interval, is constrained by a specified maximum pacing rate to be no shorter than the specified tachyarrhythmia rate threshold interval;
render the rate chamber sensing channel refractory for a selected cross-chamber sensing refractory period upon delivery of a synchronized chamber pace during which no sensing of rate chamber events occurs; and,
modify a criteria for recognizing a tachyarrhythmia so as to require a lower proportion of successive detected ventricular depolarizations when a maximum tachyarrhythmia rate threshold interval, defined as the pacing interval minus the negative offset interval, is less than a specified limit value.

14. A cardiac rhythm management device, comprising:
a sensing channel for sensing depolarizations from a heart chamber designated as the rate chamber, wherein the heart chamber contralateral to the rate chamber is designated as the synchronized chamber;
a controller for controlling the delivery of paces in accordance with a programmed pacing mode;
wherein the controller is programmed to:
detect a tachyarrhythmia when a time interval between successive rate chamber senses is below a specified first tachyarrhythmia rate threshold interval;
pace the synchronized and rate chambers with a negative offset such that the rate chamber is paced upon expiration of an escape interval and a preceding pace is delivered to the synchronized chamber at a pacing instant defined by a negative offset interval, wherein the escape interval is reset by a rate chamber pace or a rate chamber sense and wherein a pacing interval, defined as the interval between a rate chamber pace or sense and expiration of an escape interval, is constrained by a specified maximum pacing rate to be no shorter than the specified first tachyarrhythmia rate threshold interval;
render the rate chamber sensing channel refractory for a selected cross-chamber sensing refractory period upon delivery of a synchronized chamber pace during which no sensing of rate chamber events occurs; and,
increasing the pacing interval to be equal to or greater than a specified second tachyarrhythmia rate threshold interval plus the negative offset interval when an interval between a sense or pace and a subsequent sense is below the specified first tachyarrhythmia rate threshold interval.

15. A method for operating a cardiac rhythm management device, comprising:
sensing depolarizations from a heart chamber designated as the rate chamber, wherein the heart chamber contralateral to the rate chamber is designated as the synchronized chamber;
detecting a tachyarrhythmia when a time interval between successive rate chamber senses is below a specified tachyarrhythmia rate threshold interval;
pacing the synchronized and rate chambers with a negative offset such that the rate chamber is paced upon expiration of an escape interval and a preceding pace is delivered to the synchronized chamber at a pacing instant defined by a negative offset interval, wherein the escape interval is reset by a rate chamber pace or a rate chamber sense and wherein a pacing interval, defined as the time interval from an immediately preceding rate chamber sense or pace to expiration of the escape interval, is constrained to be no shorter than the specified tachyarrhythmia rate threshold interval;

rendering the rate chamber sensing channel refractory for a selected cross-chamber sensing refractory period upon delivery of a synchronized chamber pace during which no sensing of rate chamber events occurs; and, inhibiting a synchronized chamber pace at the pacing instant defined by the negative offset interval and delivering a pace to at least one of the chambers upon expiration of the escape interval when a maximum tachyarrhythmia rate threshold interval, defined as the pacing interval minus the negative offset interval, is less than a specified limit value.

16. The method of claim 15 wherein the specified limit value is the specified tachyarrhythmia rate threshold interval plus a specified safety margin.

17. The method claim of 15 further comprising delivering the synchronized chamber pace at the expiration of the escape interval, with a pace being simultaneously delivered to the rate chamber with the synchronized chamber pace, whenever the synchronized chamber pace is inhibited at the pacing instant defined by the negative offset interval.

18. The method of claim 15 further comprising delivering the synchronized chamber pace at the expiration of the escape interval, with no pace being delivered to the rate chamber with the synchronized chamber pace, whenever the synchronized chamber pace is inhibited at the pacing instant defined by the negative offset interval.

19. The method claim of 15 further comprising delivering no pace to the synchronized chamber and pace only the rate chamber upon expiration of the escape interval whenever the synchronized chamber pace is inhibited at the pacing instant defined by the negative offset interval.

20. The method of claim 15 further comprising delivering a synchronized chamber pace before expiration of the escape interval and at a time interval measured from an immediately preceding rate chamber sense or pace equal to the specified tachyarrhythmia rate threshold interval whenever the synchronized chamber pace is inhibited at the pacing instant defined by the negative offset interval.

21. The method of claim 15 wherein the rate and synchronized chambers are the right and left ventricles, respectively.

22. The method of claim 21 wherein the rate and synchronized chambers are the ventricles and further comprising pacing the rate and synchronized ventricles in accordance with a ventricular demand pacing mode such that the escape interval is a ventricular escape interval.

23. The method of claim 22 further comprising modulating the ventricular escape interval in accordance with input from an exertion level sensor.

24. The method of claim 21 further comprising pacing the ventricles in accordance with an atrial tracking mode such the escape interval is an atrio-ventricular interval.

* * * * *